United States Patent [19]

Zimmerman

[11] Patent Number: 5,265,618
[45] Date of Patent: Nov. 30, 1993

[54] SYSTEM FOR MEASURING METABOLIC GAS EMISSIONS FROM ANIMALS

[75] Inventor: Patrick R. Zimmerman, Boulder, Colo.

[73] Assignee: University Corporation for Atmospheric Research, Boulder, Colo.

[21] Appl. No.: 975,885

[22] Filed: Nov. 13, 1992

[51] Int. Cl.$^5$ .............................................. A61B 5/08
[52] U.S. Cl. .................................................. 128/718
[58] Field of Search ............................ 128/630–631, 128/716, 718

[56] References Cited

U.S. PATENT DOCUMENTS

| | | | |
|---|---|---|---|
| 4,221,224 | 9/1980 | Clark | 128/718 |
| 4,456,014 | 6/1984 | Buck et al. | 128/718 X |
| 4,640,293 | 2/1987 | Garbe | 128/716 |
| 4,830,010 | 5/1989 | Marshall | 128/630 |

FOREIGN PATENT DOCUMENTS

60-7832  1/1985  Japan .

OTHER PUBLICATIONS

Satoshi, A., "Gas Introducing Apparatus for Respiratory Gas Analyzer", EPA 0108552 published May 16, 1984.
Cammell, S. B. et al., "The Construction of Open-Circuit Calorimeters for Measuring Gaseous Exchange and Heat Production in Sheep & Young Cattle", Laboratory Practice (GB) vol. 30, No. 2 (Feb. 1981) pp. 115–119.

*Primary Examiner*—Francis Jaworski
*Attorney, Agent, or Firm*—Duft, Graziano & Forest

[57] ABSTRACT

A system is disclosed which measures the flux of metabolic gas emissions from cattle or other animals. The system does not require that the animals be confined to a chamber or stall. An animal whose metabolic gas emissions are to be measured is first fed a permeation tube (a metal tube with a gaspermeable plastic disk in one end). Inside the tube is a tracer that is physiologically inert. The permeation tube is filled with pressurized liquid tracer which slowly permeates (in gaseous form) through the plastic disk. In order to measure rumenproduced metabolic gases, a sample container, such as an evacuated container or an inflatable collar is placed on the animal. A small diameter sample tube is attached from the sample container to a halter and terminates somewhere near the animal's mouth. When the animal breathes, it exhales metabolic gases as well as the tracer. A sample of air containing both the metabolic gases and the tracer gas is then collected through the sample tube. Since the permeation rate of the tracer is known and constant, the ratio of the flux of a given metabolic gas to the flux of the tracer gas is equal to the ratio of the mixing ratios of the respective gases in the air sample that is collected. The rate of flux of metabolic gas from the animal's rumen is thus readily calculated by measuring the metabolic gas and tracer mixing ratios in the sample thus collected.

18 Claims, 4 Drawing Sheets

→ TRACE GAS
→ TRACER GAS

SYSTEM FOR MEASURING METABOLIC GAS EMISSIONS FROM ANIMALS

GOVERNMENT FUNDED INVENTION

This invention was made with government support under agreement number ATM-8709659 awarded by the National Science Foundation. The government has certain rights in this invention.

FIELD OF THE INVENTION

This invention relates generally to a system for measuring metabolic gas emissions from animals, and more particularly, to a system for measuring methane and other metabolic gas emissions from ruminant livestock without having to tether or confine the livestock.

PROBLEM

It is a problem to accurately measure energy use efficiency in cattle (or other livestock). Although scientists have developed dietary intake models to predict cattle energy use efficiency, the models must be initialized with extremely accurate information on the chemical composition and the amount of material ingested. The dietary intake models, therefore, are most useful in dairies and feed lots wherein animal diets are carefully controlled and the energy expended to gather food is minimal. The models propagate large uncertainties when applied to free-ranging cattle in unconstrained conditions. Where the cattle are free-ranging, their dietary intake is uncertain, and digestive inefficiencies can develop due to the lack of critical chemical constituents. These inefficiencies are reflected in the composition of metabolic gases expired by the animals. If the composition of the metabolic gases are known, the models can essentially be run backwards to determine the nutritional composition of the feed intake and the energy use efficiency of the animal. Dietary problems leading to poor production can thus be immediately revealed and corrected.

Scientists have conventionally determined the composition of the expired gases from livestock by selecting an animal, taming it for about forty days, feeding it a controlled diet, and then putting it in an enclosed chamber or in a headstall with the animal wearing a mask. This procedure is not only labor and resource intensive, it is also not representative of free range conditions, in which, approximately three quarters of all cattle are raised in the United States.

SOLUTION

An accurate determination of metabolic flux from ruminant animals can result in significant increases in productivity by increasing energy use efficiency. To this end, a relatively inexpensive internal tracer system has been devised which allows for metabolic flux measurement of cattle which need not be confined to a chamber or stall. The system of the present invention utilizes a tracer which is located internally within the rumen of an animal whose metabolic gas emissions such as methane, $CO_2$, $N_2O$, and the like are to be measured.

First, the animal is fed a permeation capsule (a metal capsule with a gas-permeable plastic disk in one end). Inside the capsule is a tracer that is physiologically inert, the tracer also being a compound which is neither produced nor destroyed by either the animal or its surroundings. Sulfur hexafluoride ($SF_6$) meets these requirements, and is accurately detectable in minute concentrations. Although $SF_6$ is a gas at atmospheric pressure and room temperature, it is a liquid at about 850 psig (at room temperature). The capsule is made so that the pressurized liquid $SF_6$ tracer slowly permeates (in gaseous form) through the plastic disk. The loss rate of the tracer through the plastic disk is proportional to the temperature and pressure of the tracer contained within the capsule. Since the $SF_6$ in the capsule is in a liquid state, the loss rate under a condition of constant pressure (as in the capsule) is relatively constant over long time periods. In addition, since an animal's internal digestive tract temperature is relatively constant, the loss rate of the tracer from the capsule is also constant.

Next, a collection vessel, such as an evacuated container or an inflatable collar, is placed on the animal order to collect a sample of the metabolic gases produced in the digestive tract. The present invention can function with either a small pump (for inflating a collar with gas samples), or rely on a vacuum in the container to draw a sample through a flow-controlling restrictor into the container at a constant rate. A small diameter tube is attached from the collar to a halter and terminates somewhere near the animal's mouth. When the animal breathes, it exhales metabolic gases including methane, as well as the tracer. A sample of these gases is continuously collected and stored in the collection vessel.

Analysis of the sample is straightforward, since the loss rate of the tracer is known and constant, the ratio of the concentration of the metabolic gas to the concentration of the tracer in the air sample that is collected is equal to the ratio of the fluxes of the respective gases. It is not necessary to sample directly inside the animal's mouth or to sample every breath. The internal tracer release system can also be used with instrumentation located in a backpack worn by the animal whose trace gas emissions are to be measured. Analysis of the collected gas sample can be performed in real-time by the backpack instrumentation, and the results of the analysis transmitted to a remote receiving facility.

In addition to its use in establishing methane and other metabolic gas emission rates from ruminants, the tracer system of the present invention is very beneficial in rumen metabolic studies. For example, methane production by the rumen microflora has long been recognized as an inefficiency in dietary energy utilization. Many efforts have been made to depress this loss and shunt the carbon and metabolic hydrogen to more productive end-products of fermentation. Available techniques to measure methane losses are expensive and allow only very small numbers of animals to be studied. The present tracer system alleviates this problem and should allow easy evaluation of new methods for manipulating rumen fermentation. This in turn will help identify those feeding systems which allow the most efficient use of dietary energy for maintenance or growth of animals.

DETAILED DESCRIPTION OF THE INVENTION

Figure 1:
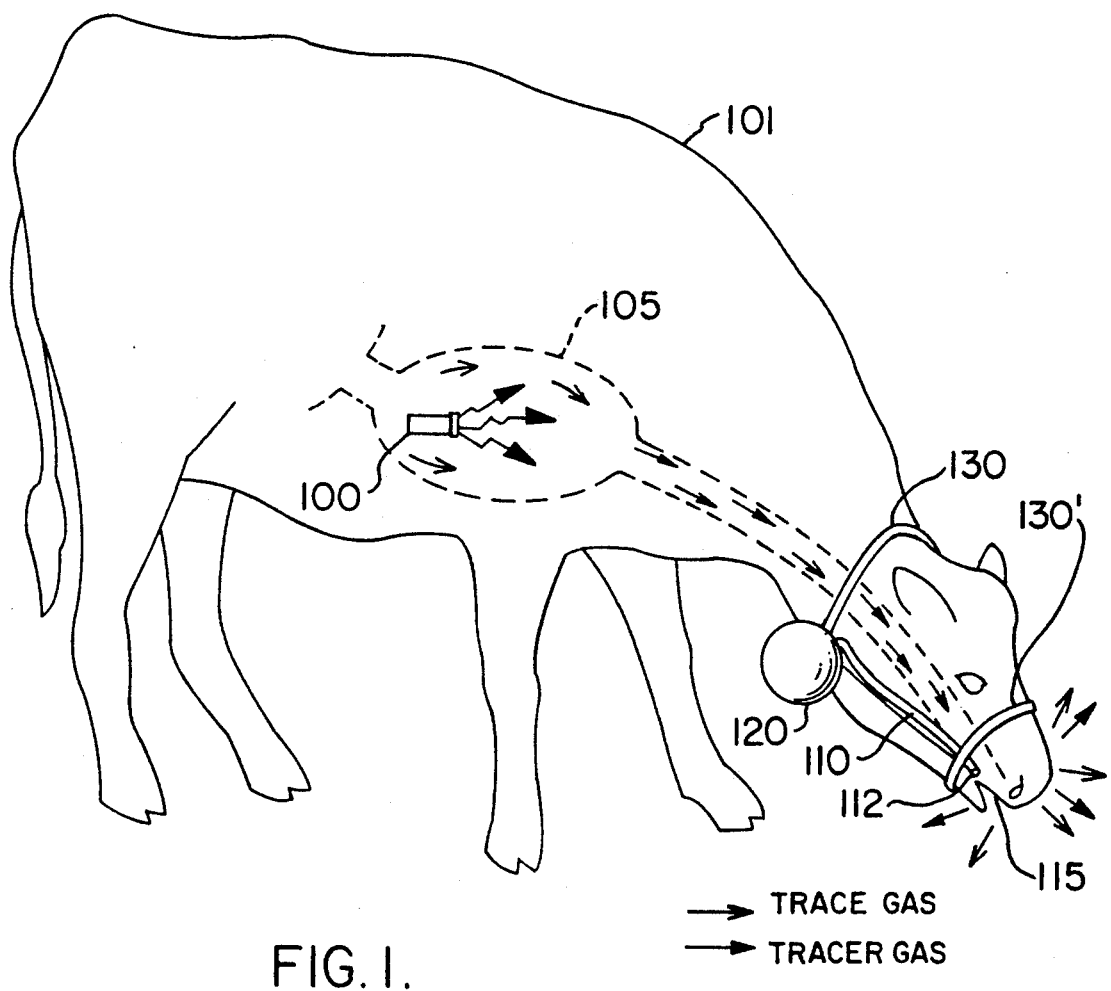
FIG. 1 is a cut-away view of a cow, showing an embodiment of the present invention wherein a permeation capsule is placed in the cow's rumen, and a gas inlet tube and sample container is attached to the cow via a harness.

FIG. 1 illustrates an exemplary embodiment of the present invention wherein a permeation capsule 100 is placed in a cow's rumen 105, and a gas inlet tube 110 and sample container 115 are attached to the cow 101 via a harness 120. In this particular embodiment, permeation capsule 100 functions as a point source emitter 100 of a known tracer gas. Permeation capsule 100 produces an output that consists of an easily measured gas released at a very precisely controlled rate. In this particular embodiment, capsule 100 (also referred to as an "ampoule") has a permeable membrane through which the tracer gas is emitted. The permeation capsule 100 is swallowed by a ruminant or other animal 101 to measure the rate of methane and other metabolic gas emissions from the rumen 105 or digestive tract of the animal 101. These metabolic gases are expelled from the animal 101 by eructation, or belching.

The gas collection apparatus used in this embodiment consists of a tracer gas and metabolic gas collection apparatus 110, 120, 130 which is affixed around the neck of the animal 101. The actual rate of metabolic gas emissions can be precisely determined by measuring both the metabolic gas and tracer gas collected and using this data to calculate the dilution factor, since the rate of tracer gas release is a fixed and known quantity. By multiplying this dilution factor by the measured metabolic gas emissions, the rate of metabolic gas production can be very precisely calculated on an ongoing basis.

RUMEN CHARACTERISTICS

The rumen 105 is an anaerobic fermentation vat which contains a stable population of microbes and protozoa that interact to ferment plant material, converting it to products that the ruminant animal 101 can then use to meet its own nutritional needs. It is considered an open and continuous ecosystem because of the constant supply of nutrients through ingestion of food and water by the animal 101 and the continuous removal of end products of fermentation either by absorption across the rumen wall or passage out of the rumen 105. Rumen temperature is maintained at a relatively stable 35° C. to 42° C. by heat of fermentation and normal aerobic tissue metabolism, and pH is maintained between 5.7 and 7.3 by copious salivary secretions of bicarbonate and phosphate that neutralize the fermentation acids. Mixing is constant because of rumen wall contractions which occur at one to two-minute intervals, while the low oxygen concentration and redox potential (Eh=0.25 to =0.45 mV) provide a stable environment for obligate or facilitative anaerobes.

Methane, carbon dioxide, and other metabolic gases produced in the rumen 105 may be discharged in two ways. The predominant method is eructation, although during periods prior to feeding 25-94% of the methane produced may be absorbed through the rumen wall into the blood and cleared from the lungs (Hoernecke et al., "Composition and absorption of rumen gases and their importance for the accuracy of respiration trials with tracheotomized ruminants," Symposium on Energy Metabolism, EAAP, 1964). After feeding, estimates of absorbed methane drop to approximately 20%.

PRINCIPLE OF THE INVENTION

The metabolic gas emission tracing system for animals consists of a tracer gas emitter and a collection apparatus 110, 120, 130. In an exemplary embodiment, the tracer gas emitter consists of a capsule 100 (ampoule) that can be ingested by the animal 101 whose metabolic gas emissions are to be measured. These metabolic gas emissions are shown in FIG. 1 as arrows labelled "trace gas". Because the internal temperature of the animal is essentially constant, the capsule 100 is placed in a constant temperature environment and emits a tracer gas at a controlled, predetermined rate through a permeable membrane 240 contained in the capsule 100. Tracer gas is shown in FIG. 1 by solid arrows. This tracer gas mixes with the metabolic gas emissions from the rumen/digestive tract 105 of the animal and is emitted into the atmosphere as a result of eructation. The gas collection apparatus 110, 120, 130 is mounted, for example, on a collar 130 worn by the animal. This collection apparatus 110, 120, 130 collects air samples containing both the metabolic gases and the tracer gas originating in the animal's digestive tract. In the case of a ruminating animal such as a cow 101, for example, the metabolic gases and tracer originate in the animal's rumen 105. A detector (not shown), typically located in a laboratory, measures the level of metabolic gas in each collected sample as well as the concentration of tracer gas associated therewith. In an alternative embodiment described below, a detector may be attached to the animal in order to provide real-time metabolic gas measurements which can be transmitted to a remote recording facility.

Since the permeation capsule or other tracer gas emitter produces tracer gas at a predetermined rate, measuring the amount of tracer gas located in the ambient air at the inlet 112 of the collection apparatus 110, 120, 130 allows a precise determination to be made of the dilution of the metabolic gases as they pass from the digestive tract of the animal 101 to the surrounding atmosphere. Therefore, by using a simple ratio calculation, the actual rate of metabolic gas emission from the animal 101 can be determined based on the metabolic gas mixing ratio measured at inlet 112, multiplied by the rate of tracer gas emission (from the tracer gas emitter), divided by the tracer gas mixing ratio measured at inlet 112. This concept works well with any source of emissions wherein the dispersion path of the emissions is the same as that of the trace gas(es).

The flux of methane or other metabolic trace gas that is produced by an animal 101 can be determined from the ratio of the concentrations of the metabolic gases measured near the animal's mouth to the concentration of the tracer gas also measured near the mouth, multiplied by the known emission rate of the tracer from the tracer emitter.

The following equation snows the principle by which the flux of a metabolic gas originating in the digestive tract of an animal 101 can be determined from an ambient air sample:

$$F = F_t \cdot G_c / G_t$$

F = F * G /G
Where:
F = Flux of metabolic gas
$F_t$ = Flux of tracer gas
$G_c$ = Mixing ratio of metabolic (trace) gas in sample, and
$G_t$ = Mixing ratio of tracer gas in sample

TRACER GAS CHARACTERISTICS

Sulfur Hexafluoride, $SF_6$, is widely used as an atmospheric tracer gas because of the extremely low detection limit and simplicity of analysis. The gas is non-toxic, inert, colorless, odorless, and relatively inexpensive. The gas has been used previously in lung-function studies in dogs and rabbits (Lester and Greenberg, "The toxicity of sulfur hexafluoride," *Arch. Indust. Hvg. Occup. Med.* 2:348-349, 1950) where $SF_6$ was used to replace nitrogen in breathing air (i.e., at 80% concentration). No toxic effects were observed in these studies. $SF_6$ has been tested in artificial rumen studies. These studies indicate no measurable impact on rumen flora, the production of volatile fatty acids, or metabolic gas production.

TRACER PERMEATION CAPSULE

Figure 2:
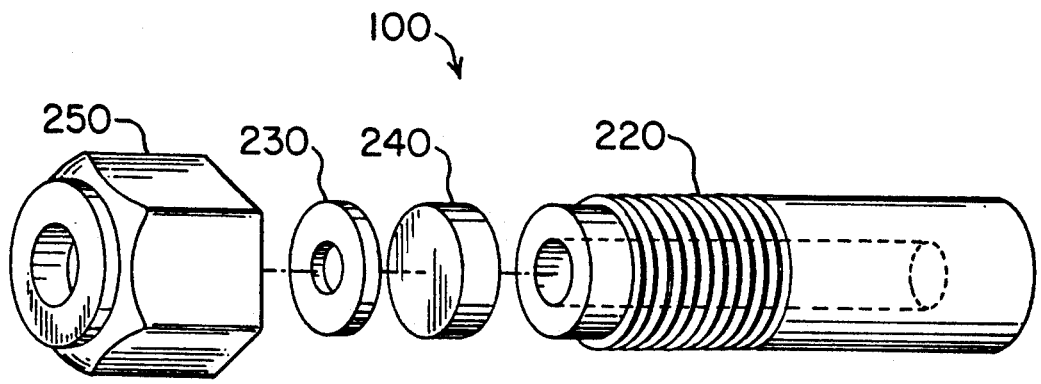
FIG. 2 is a diagram of a permeation capsule used to emit a tracer gas.

FIG. 2 is a diagram of a permeation capsule 100 used by the present invention to emit a tracer gas. In accordance with the present invention, a small permeation capsule (ampoule) containing a tracer comprising sulfur hexafluoride ($SF_6$) is inserted into the rumen 105 of a cow. Air samples collected near the cow's mouth are analyzed for $SF_6$, methane, carbon dioxide, and other metabolic trace gases. By knowing the tracer gas release rate in the rumen 105, the ratio of measured concentrations can be used to calculate the trace gas emission rate. This can be done without measuring breathing or air exchange rates in the rumen 105 because both the trace gas and tracer gas are diluted in the air to the same extent. This method eliminates the need to sample directly from the animal's throat since changes in dilution associated with head movement or ambient winds are accounted for directly with the tracer method of the present invention.

The $SF_6$ permeation capsule to be used in this method is typically constructed from a $\frac{3}{8}$" stainless steel rod approximately $1\frac{1}{4}$ inches long. This rod is drilled from one end to within approximately $\frac{1}{8}$" of the other end, thereby forming a tube 220 with a closed end. The open end of the tube 220 is threaded and capped with an approximately 0.06" thick teflon disk 240 held in place with a washer 230 and a standard $\frac{3}{8}$ Swagelok nut 250. The teflon disk 240 is, for example, TFE teflon, but it is to be understood that other inert permeable materials could also be used. Tube 220 is filled cryogenically with liquid $SF_6$ and then allowed to equilibrate to typical rumen temperature in a water bath.

The rate of tracer gas permeation through disk 240 can be assigned in two ways—(1) maintaining the temperature of the tube 220 at rumen temperature and repeated weighing of the tube 220 on a precision balance over a several week period and (2) periodically measuring the loss rate by maintaining the temperature of the tube 220 at rumen temperature and measuring the concentration of $SF_6$ in dilution air passed over the tube 220 at a uniform rate. Typical permeation rates are on the order of 30 nanograms/minute and, under relatively constant ambient temperatures, as found in the field, the permeation rates are extremely stable.

TRACER/METABOLIC GAS SAMPLING APPARATUS

Three embodiments of gas sampling apparatus are disclosed herein. Each of these embodiments is attached to the animal 101 via a harness 130 (and an optional harness 130'). These embodiments include (1) one or more small evacuated chambers, each fitted with a flow-controlling orifice; (2) a small battery powered pump connected to one or more small bags; and (3) a real-time, continuous sampling analyzer.

As shown in FIG. 1, in one exemplary embodiment of the gas sampling apparatus of the present invention, tracer/metabolic gas samples are collected using a sample container 120 typically comprising an evacuated stainless steel sphere 120 which is attached to a collar 130 located around the animal's neck. A gas inlet tube 110, typically $\frac{1}{8}$" I.D., is attached to the animal by means of a back-pack (not shown) or a harness 130' placed around the animal's head. One end of gas inlet tube 110 is attached to sphere 120, and the other end of gas inlet tube 110 terminates somewhere near the animal's mouth. More than one of these spheres 120 (or other types of gas sample containers) may be connected to gas inlet tube 110, in which case a timer circuit (not shown) is used to control which sphere 120 receives a gas sample, as well as when a sample is introduced into a given sphere 120. This timer circuit functions in accordance with the multiple-bag gas collection apparatus described below.

Figure 3:
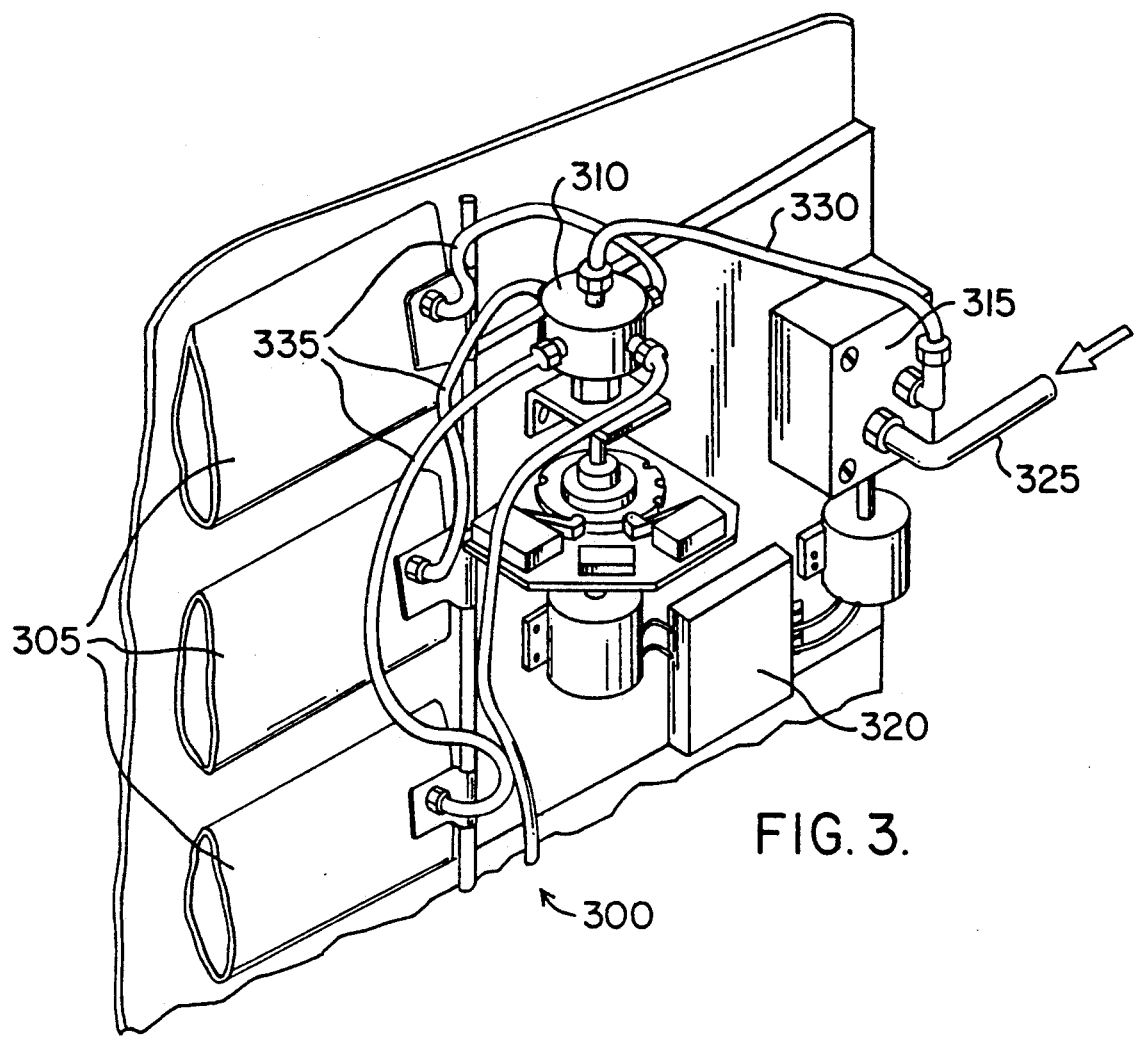
FIG. 3 is a perspective view of a multiple-bag gas collection apparatus including a battery powered pump, selector valve and timer control circuit.

FIG. 3 is a perspective view of a multiple-bag gas collection apparatus 300 including a battery powered pump 315, selector valve 310 and timer circuit 320. In this embodiment, a small pump 315 is used to fill a selected Teflon bag 305 over a predetermined time to obtain a time-averaged air sample. The air sample thus obtained can be quickly and accurately analyzed for tracer using a portable electron capture gas chromatograph (not shown). The detection limit of a suitable chromatograph is approximately ten parts per trillion (10 ppt). Multiple-bag gas collection apparatus 300 is described in greater detail below.

Figure 7:
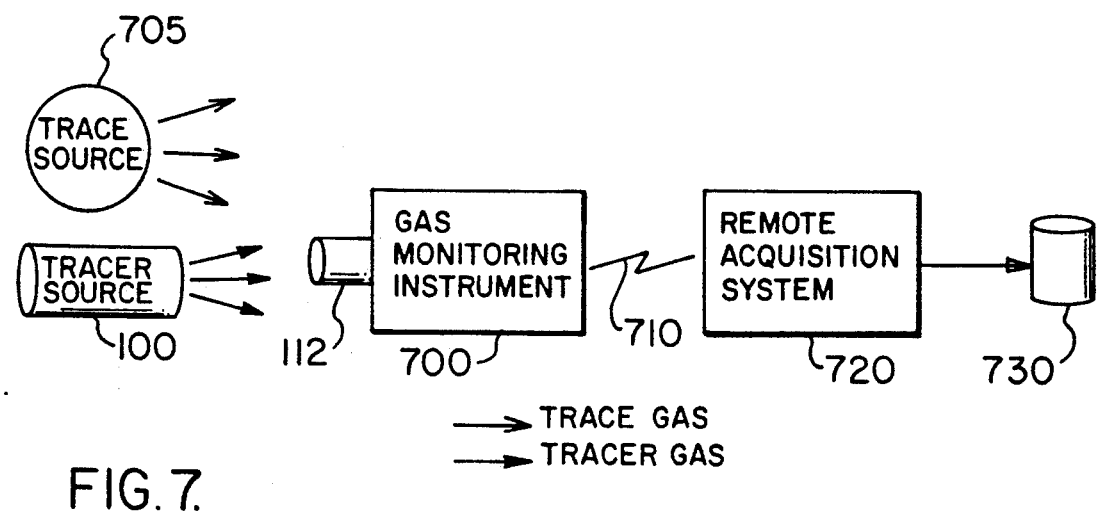
FIG. 7 illustrates an embodiment of the sampling apparatus which uses real-time gas monitoring apparatus to measure the concentrations of gases produced by an animal or other trace gas source.

FIG. 7 illustrates an embodiment of the sampling apparatus which uses real-time gas monitoring apparatus 700 to measure the concentrations of gases produced by an animal or other trace gas source 705. Gas measurement data is transmitted to a remote site 720 for analysis in order to simplify the process of data acquisition.

1. Stainless Steel Sample Collection Sphere

Figure 4:
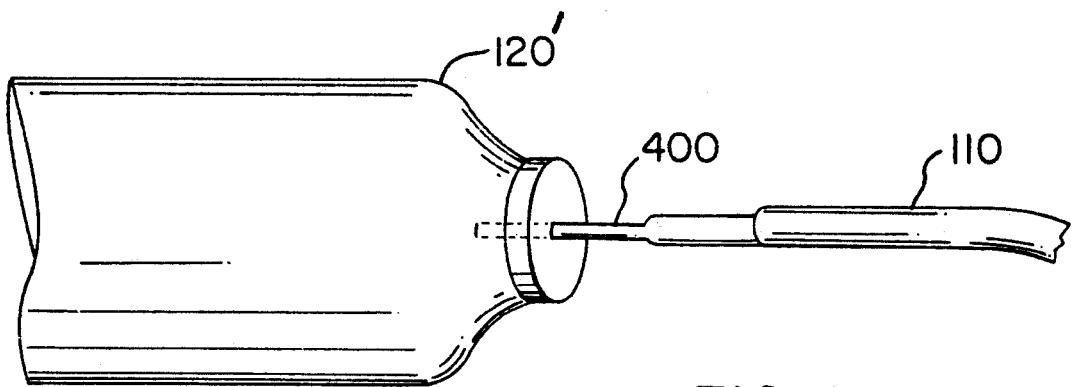
FIGS. 4 through 6 illustrate alternate embodiments of apparatus used for flow rate restriction.
Figure 5:
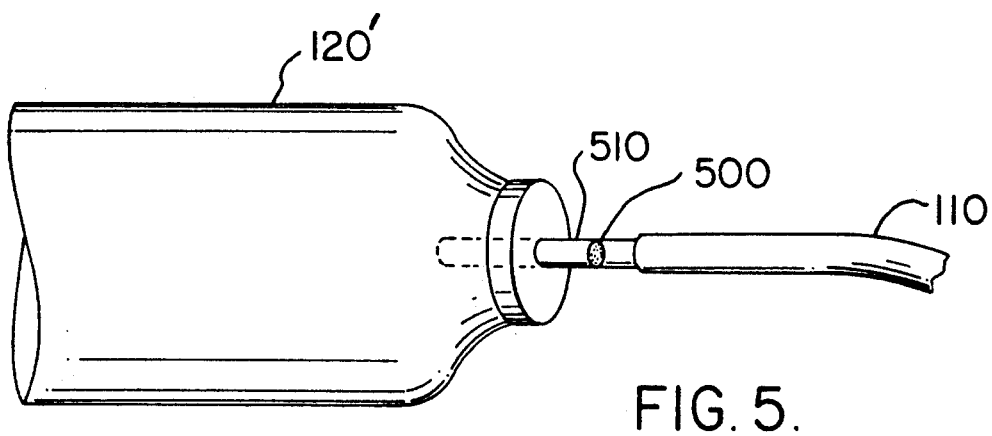
Figure 6:
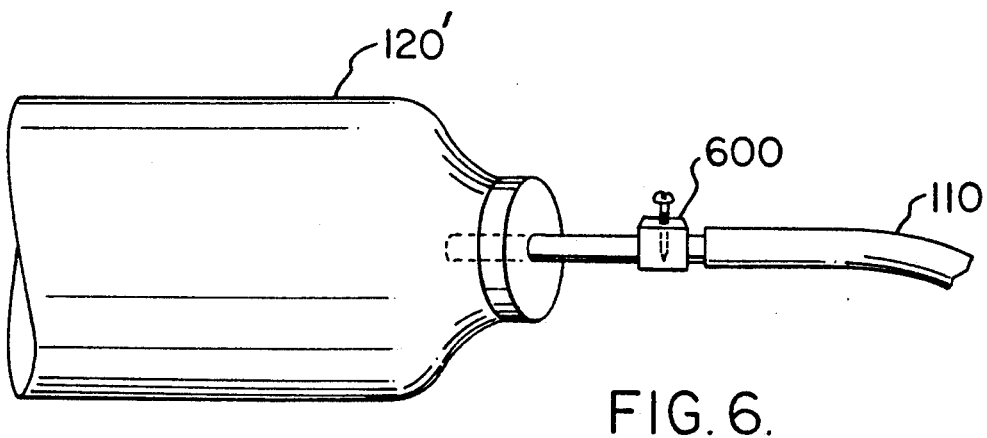

One type of sample collection container which can be used to sample metabolic gases from an animal 101 is a gas sample container comprising an electropolished stainless steel sphere 120 which has been evacuated to a pressure of typically a few microns. The volume of the sample collection sphere 120 is not critical, and in practice may vary from approximately 0.25 liters to 5 liters. Sample collection spheres 120 having a volume of approximately 0.5 liters have been used in the field, with good results. The flow rate of the gas sample into the evacuated sphere 120 is held constant by one of several alternative types of apparatus described below. Each type of apparatus employs a gas flow restricting mechanism which is attached between gas inlet tube 110 and sample collection sphere 120 or other sample container 120'. FIGS. 4 through 6 illustrate alternate embodiments of apparatus used to restrict the rate of gas flow into an evacuated collection container 120'. As shown in FIG. 4, one type of apparatus for providing a constant restricted gas flow rate employs a capillary restrictor tube 400 having a narrow inner diameter, for example, 0.13 millimeters (0.005 inches). As long as the pressure differentiated in the sample collection sphere 120 or sample container 120, is at least 0.5 atmospheres, the flow rate will remain constant. The sample integration time can be adjusted by varying the length and inside diameter of the restrictor tube 400.

Figure 8:
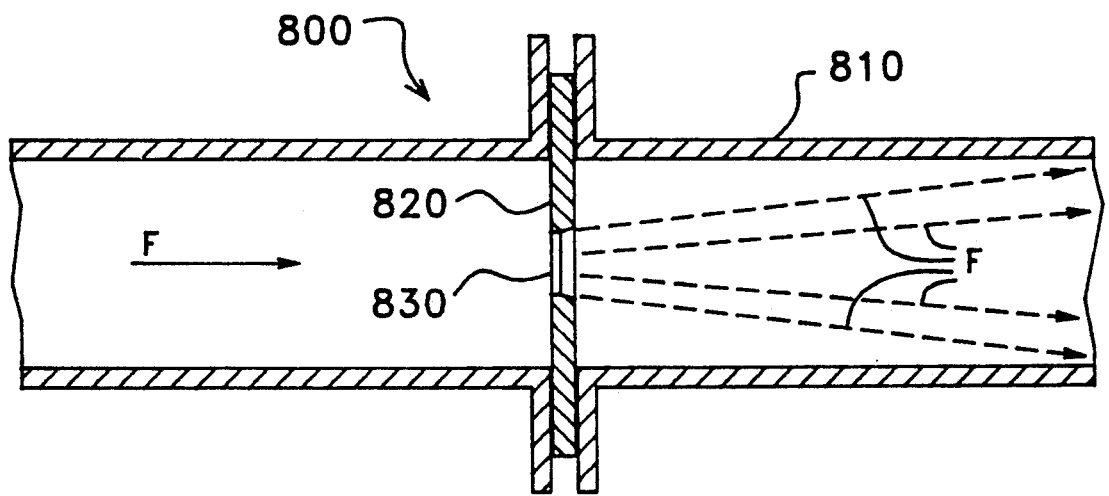
FIG. 8 is a cross-sectional view of a critical flow orifice.

FIG. 8 is a cross-sectional view of a critical flow orifice 800 which can also be used to obtain constant flow into a sample collection sphere 120 or other sample collection container 120'. A critical flow orifice comprises, for example, a tube 810 containing a flat plate 820 perpendicular to the gas flow F in which a relatively small sharp-edged hole 830 is bored. The rate of flow of gas through the hole 830 becomes constant once the pressure differential is sufficient so that the linear velocity of the gas molecules in the throat of the orifice reaches the speed of sound. Critical flow orifices are well-known in the art. See, for example, "Handbook of Vacuum Physics", pp. 5-11-5-14 (Beck, Pergammon Press, 1966), and "Chemical Engineers, Handbook", pp. 255-56 (Perry and Chilton, McGraw-Hill, 1978).

As shown in FIG. 5, another type of apparatus for restricting the gas flow rate into evacuated collection container 120 employs a restrictor made from a porous sintered frit 500. Frit 500 is located in a tube connected between gas inlet tube 110 and collection container 120. This porous frit 500 is typically pressed into a Swagelok ® fitting such as a ⅛ inch brass union. Porous frit 500 also provides a constant flow over a pressure drop greater than 0.5 atmospheres.

As shown in FIG. 6, yet another type of apparatus for flow rate restriction employs a needle valve assembly 600 which allows for adjustment of the gas flow rate. It is to be understood, however, that equivalent results are obtainable by using evacuated containers 120 made from relatively inert materials other than stainless steel, and by using containers 120 having non-spherical shapes. Equivalent results may also be obtained from the use of gas flow rate control mechanisms other than those described above.

2. Multiple Bag Sample Collection System

As shown in FIG. 3, a further exemplary embodiment of the apparatus used to sample metabolic gases is a gas collection apparatus 300 which is worn around the animal's neck. Gas collection apparatus 300 is comprised of a plurality of small (approximately 5 liter) teflon sample bags 305 connected to a selector valve 310 which is connected to a small pump 315. Pump 315 is, for example, a teflon-head battery-powered pump which sequentially fills the bags 305. Pump 315 draws an atmospheric sample into inlet 325 and directs the sample along feed tube 40 to selector valve 310. Selector valve 310 determines which one of the sample bags is connected to the sample flowing through feed tube 330. A timer circuit 320 is used to actuate pump 315 which fills a selected sample bag 305 at a predetermined flow rate, via supply tubes 335. Timer circuit 320 also causes selector valve 310 to connect feed tube 330 to the appropriate supply tube 335. The number of bags 305 can be adjusted from four to as many as 24 or more, so that a plurality of averaged samples can be collected over a diurnal feeding cycle.

This gas collection apparatus 300 is used for measurements of free-range cattle, wherein the measurements are made under more realistic circumstances than those made using a confined animal. The gas collection apparatus 300 of the present embodiment thus produces more accurate results than measurements made using conventional techniques with confined cattle.

3. Continuous Sampling/Transmitting Analyzer

An additional exemplary embodiment of the gas sampling apparatus of the present invention employs a miniaturized monitoring instrument 700 capable of continuously measuring trace gases such as methane and carbon dioxide, as well as a tracer gas. Monitoring instrument 700 is worn around the neck of the animal 101 in the same fashion as gas collection apparatus 110,120,130. Real-time gas monitoring instrument 700 takes ambient air samples containing both trace gas and tracer gas. Measurements of the relative concentrations of tracer gas and trace gas in the sample are then transmitted via a communication link 710 to a remote acquisition system 720 where they are stored on recording media 730 in order to be further analyzed to produce, for example, reports used for optimization of supplementary cattle feed.

Monitoring instrument 700 may also collect other metabolic data, such as breathing rate and heartbeat rate and body temperature.

Laboratory Gas Analysis

Collection sphere or bag samples are analyzed in a laboratory for methane, carbon dioxide, and other gases, using a temperature controlled gas chromatograph, for example, a Baseline Industries Model GC, fitted with a six-port gas sampling valve, a stainless steel column packed with molecular sieve (5A), a catalytic reduction oven which reduces $CO_2$ to $CH_4$, and a flame ionization detector with a detection limit of 50 ppb (parts per billion) of methane. The system of the present invention is calibrated with certified commercial mixtures of methane and carbon dioxide in air.

Prior art gas measurement systems typically consist of apparatus that separates the desired gas from its ambient environment in order to measure the quantity of the gas that is present. Prior art systems typically use an enclosure placed over the animal to measure metabolic gas fluxes. In the case of ruminants, such as cows, this requires that the ruminant be placed in an enclosed chamber or in a headstall. This artificial environment is not applicable to the problem of measuring metabolic gas emissions from free range animals. Alternatively, prior art flux calculations based on ambient measurements are inaccurate due to variable mixing of the air and the metabolic gases caused by winds. In the case of ruminants, the source of the emissions is the digestive tract of the animal and these emissions occur randomly as a result of eructation. The path over which these gas emissions travel is tightly constrained while within the animal, but once they reach the animal's mouth, dispersion is random and uncontrolled. The difficulty with measuring these emissions is complicated by the fact the measuring apparatus must be located in close proximity to the mouth of the animal in order to obtain an accurate measurement. By constraining the movements and diet of the animal, the validity of the data produced is compromised. Therefore, prior art methods of measuring emissions are inaccurate because they create an artificial environment in which the subject animal is placed, which environment affects the process that is to be measured. There is no known prior art method for measuring methane emissions that has any credible degree of accuracy for unconstrained, free-ranging animals.

The present invention is of significant commercial importance because the rate of methane emissions and the various other metabolic gases emitted by an animal bears a direct relationship to the digestive efficiency of the animal. Therefore, by closely monitoring a selected group of cattle within a herd, the digestive efficiency of the herd can be monitored on a continuing basis. This enables the herd manager to adjust the contents of the food source in order the minimize the cost of feed and maximize the meat or milk production. The tracer system of the present invention is highly efficient since the tracer gas emitter 100 is easily inserted into the animal, and the collection/analysis apparatus 110, 120, 130 (or apparatus 300 or 700) is unobtrusively worn around the neck of the animal. Furthermore, this tracer system can transmit the results of the metabolic gas analysis to a remote acquisition system 720 on a realtime basis. The system of the present invention has wide commercial applicability and provides a very cost effective measurement tool that enables beef and milk producers to pro-actively intervene in the feeding regimen of their animals.

Of primary importance is the fact that the present invention directly yields a metabolic gas flux which is representative of a large group of cattle under real world conditions. It is no longer necessary to extrapolate from single-cow, energy balance experiments.

It is to be expressly understood that the claimed invention is not to be limited to the description of the preferred embodiment but encompasses other modifications and alterations within the scope and spirit of the inventive concept.

I claim:

1. A system for sampling and measuring a rate of emission of a metabolic trace gas from an animal comprising:
   means, adapted to be placed internally within a digestive tract of said animal, for releasing a tracer gas at a known rate of flux;
   sampling means, external to said animal, for collecting a sample containing both said tracer gas and said trace gas emitted from said animal.

2. The method of claim 1, further including:
   means, utilizing said sample, for determining said rate of emission of said trace gas from said animal.

3. The system of claim 1, wherein said means for releasing a tracer gas includes:
   a non-gas-permeable vessel, said vessel containing a pressurized quantity of said tracer gas, said vessel having a gas-permeable member through which said tracer gas can flow at a known rate of flux.

4. The system of claim 1, wherein said sampling means includes:
   a length of tubing, said tubing having a first end and a second end, said tubing being positioned such that said first end of said tubing is in proximity to the mouth of said animal;
   a pump for drawing air through said tubing, said pump having an intake port and an exhaust port, said intake port being connected to said second end of said tubing;
   a selector valve connected to said exhaust port of said pump;
   a plurality of inflatable containers, each of said inflatable containers being switchably connected, via said selector valve, to said exhaust port of said pump; and
   a timed controller, connected to said selector valve, for controlling, at predetermined time intervals, a connection between said exhaust port of said pump and a desired one of said plurality of inflatable containers.

5. The system of claim 1, wherein said sampling means includes:
   a length of tubing, said tubing having a first end and a second end, said tubing being positioned such that said first end of said tubing is in proximity to the mouth of said animal; and
   at least one evacuated container connected to said second end of said tubing.

6. The system of claim 5, wherein a capillary restrictor tube having a narrow inner diameter is connected between said second end of said tubing and said evacuated container to provide a constant restricted gas flow rate into said evacuated container.

7. The system of claim 5, wherein a restrictor made from a porous sintered frit is located in a tube connected between said second end of said tubing and said evacuated container to provide a constant restricted gas flow rate into said evacuated container.

8. The system of claim 5, wherein a needle valve is connected between said second end of said tubing and said evacuated container to provide an adjustable gas flow rate into said evacuated container.

9. The system of claim 5, wherein a flat plate having a relatively small diameter sharp-edged orifice is located in a tube connected between said second end of said tubing and said evacuated container to provide a constant restricted gas flow rate into said evacuated container.

10. The system of claim 1, further comprising:
    means, responsive to said sampling means, for transmitting, to a remote site, values indicative of a mixing ratio of said trace gas and a mixing ratio of said tracer gas.

11. The system of claim 1, wherein said determining means includes:
    means, connected to said sampling means, for measuring a mixing ratio of said trace gas and a mixing ratio of said tracer gas;
    means, connected to said measuring means, for transmitting values indicative of said mixing ratio of said trace gas and of said mixing ratio of said tracer gas;
    means, located remotely from said animal, for receiving said values transmitted by said transmitting means; and
    means, responsive to said values received by said receiving means, for calculating a rate of emission of said trace gas from said animal.

12. The system of claim 11, wherein said calculating means calculates said rate of emission of said trace gas according to the formula:

$$F = F_t * G_c / G_t$$

where $F$ = said rate of emission of said trace gas, $F_t$ = said known rate of flux of said tracer gas, $G_c$ = a mixing ratio of said trace gas, and $G_t$ = a mixing ratio of said tracer gas.

13. The system of claim 1, wherein said sampling means is attached to said animal.

14. A system for measuring a rate of emission of a metabolic trace gas from an animal, said system having a self-contained news placed internally within a digestive tract of said animal for releasing a tracer gas at a known rate of flux comprising:
sampling means adapted to be attached externally to said animal, for collecting a sample containing both said tracer gas and said trace gas emitted from said animal; and
means, utilizing said sample, for determining said rate of emission of said trace gas from said animal.

15. A method of measuring a rate of emission of a metabolic trace gas from an animal comprising the steps of:
placing in a digestive tract of said animal; a first device for releasing, at a known rate of flux, a tracer gas;
collecting, via a second device attached externally to said animal, a sample of ambient air containing both said tracer gas and said trace gas; and
determining said rate of emission of said trace gas from said animal by calculating a ratio of a mixing ratio of said trace gas in said sample to a mixing ratio of said tracer gas in said sample, multiplied by said known rate of flux of said tracer gas.

16. The method of claim 15, wherein the step of determining includes transmitting, to a remote analyzer, values indicative of mixing ratios of said trace gas and said tracer gas in said samples.

17. A method of measuring metabolic trace gas emissions from a ruminating animal, said animal having a rumen for digesting food, comprising the steps of:
placing in said rumen of said animal, a gas emitting device for releasing, at a known rate, a tracer gas;
collecting, from a device attached externally to said animal, contemporaneous samples of both said tracer gas and said trace gas emissions; and
determining a rate of emission of said trace gas from said rumen of said animal, utilizing said samples of said tracer gas and said trace gas.

18. The method of claim 17, wherein the step of determining includes transmitting, to a remote site, values indicative of mixing ratios of said trace gas and said tracer in said samples.

* * * * *